(12) United States Patent
Chen et al.

(10) Patent No.: US 8,501,459 B2
(45) Date of Patent: Aug. 6, 2013

(54) TEST PROBES, COMMON OLIGONUCLEOTIDE CHIPS, NUCLEIC ACID DETECTION METHOD, AND THEIR USES

(75) Inventors: Chao Chen, Shaanxi (CN); Yitong Tang, Shaanxi (CN); Yali Cui, Shaanxi (CN); Juanli Zhu, Shaanxi (CN); Longlin Yu, Shaanxi (CN); Yiwen Gao, Shaanxi (CN); Zheng Li, Shaanxi (CN)

(73) Assignee: Shaan Xi Lifegen Co., Ltd., Shaanxi (CN)

( * ) Notice: Subject to any disclaimer, the term of this patent is extended or adjusted under 35 U.S.C. 154(b) by 68 days.

(21) Appl. No.: 12/994,017

(22) PCT Filed: Oct. 6, 2008

(86) PCT No.: PCT/CN2008/001695
§ 371 (c)(1),
(2), (4) Date: Mar. 14, 2011

(87) PCT Pub. No.: WO2009/140802
PCT Pub. Date: Nov. 26, 2009

(65) Prior Publication Data
US 2011/0218115 A1     Sep. 8, 2011

(30) Foreign Application Priority Data

May 23, 2008    (CN) .............................. 2008 1 009770

(51) Int. Cl.
*C12M 1/34*     (2006.01)
*C12M 3/00*     (2006.01)
*C12Q 1/68*     (2006.01)
*C12C 19/34*    (2006.01)
*C07H 21/02*    (2006.01)
*C07H 21/04*    (2006.01)

(52) U.S. Cl.
USPC ........ 435/287.2; 435/6.1; 435/6.11; 435/6.12; 435/91.1; 435/91.2; 536/23.1; 536/24.3; 536/24.33

(58) Field of Classification Search
USPC ........... 435/6.1, 6.11, 6.12, 91.1, 91.2, 91.51, 435/183, 283.1, 287.1, 287.2; 436/94, 501; 536/23.1, 24.3, 24.33, 25.3
See application file for complete search history.

(56) References Cited

U.S. PATENT DOCUMENTS

| | | | |
|---|---|---|---|
| 2003/0032016 A1* | 2/2003 | Barany et al. ..................... 435/6 |
| 2008/0124810 A1* | 5/2008 | Terbrueggen ..................... 436/94 |

* cited by examiner

*Primary Examiner* — Frank Lu
(74) *Attorney, Agent, or Firm* — Nath, Goldberg & Meyer; Joshua B. Goldberg; Megan B. Doughty

(57) ABSTRACT

High-throughput detection for the interesting base or the mutation site in the nucleic acid sample can be achieved by means of the linear test probe pairs P1 and P2. The test probe pairs P1 and P2 respectively comprise either of the flanking complementary sequences which are adjacent to the interesting base or the mutation site in the nucleic acid sample. The invention can be applied to the re-sequencing the target nucleic acid sequence, the detection and analysis for the mutation, insertion, or deletion sites of a known nucleic acid sequence, and the genotyping of the pathogenic microorganism.

9 Claims, 9 Drawing Sheets

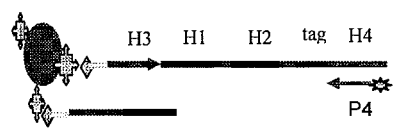
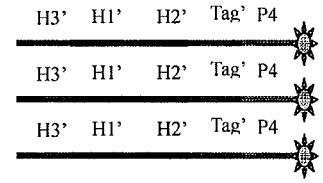
Fig. 2E                Fig. 2F
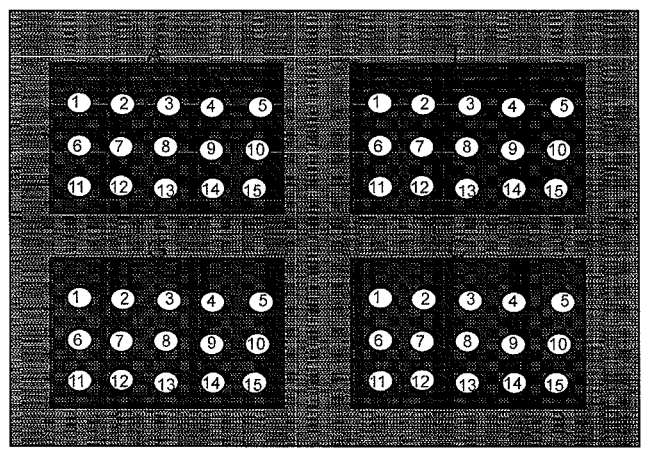
Fig. 3
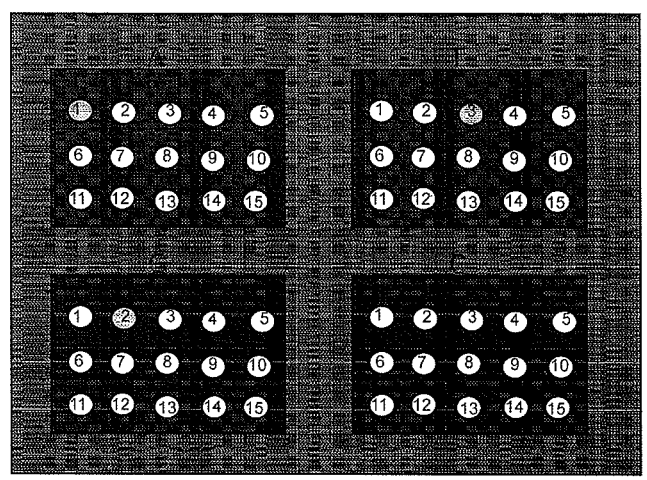
Fig. 4

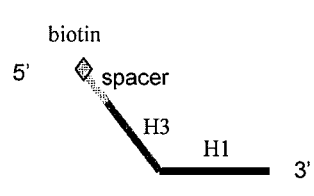
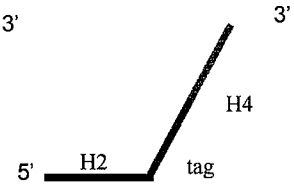
Fig. 6A    Fig. 6B    Fig. 6C
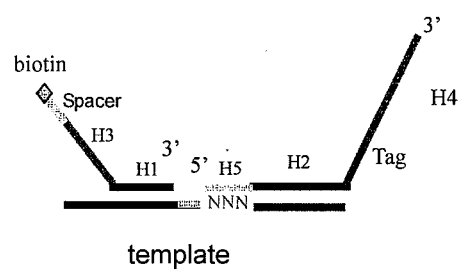
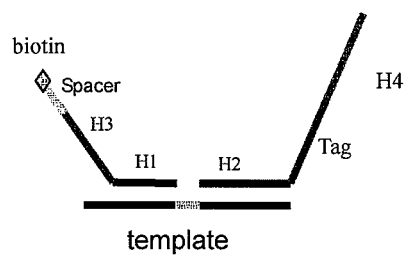
Fig. 7A    Fig. 7B
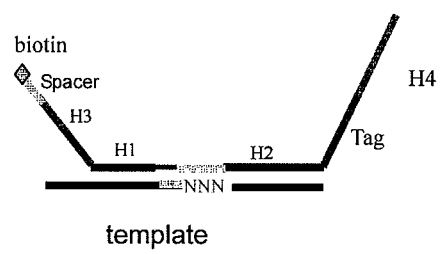
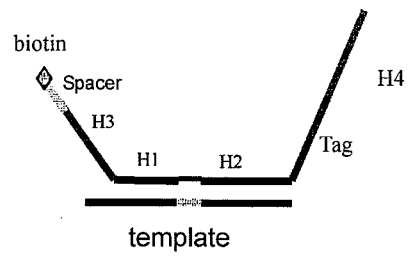
Fig. 7C    Fig. 7D

SEQUENCE LISTING

```
<160> NUMBER OF SEQ ID NOS: 5

<210> SEQ ID NO 1
<211> LENGTH: 53
<212> TYPE: DNA
<213> ORGANISM: Artificial Sequence
<220> FEATURE:
<223> OTHER INFORMATION: synthesized detection probe P1
<221> NAME/KEY: modified_base
<222> LOCATION: (1)
<223> OTHER INFORMATION: n=thymidine modified by biotin molecule

<400> SEQUENCE: 1
nttttttggg ttcgtggtag agcgtcggag tgagagagtc gatgttcact cca          53

<210> SEQ ID NO 2
<211> LENGTH: 71
<212> TYPE: DNA
<213> ORGANISM: Artificial Sequence
<220> FEATURE:
<223> OTHER INFORMATION: synthesized detection probe P2
<221> NAME/KEY: modified_base
<222> LOCATION: (1)
<223> OTHER INFORMATION: n=adenosine modified via phosphorylation

<400> SEQUENCE: 2
ntgatgtgct agtgatcaca tccgccgtgt ctgccgctgg gttatcaggc tgctatctcg    60
gtgtcgtctg g                                                         71

<210> SEQ ID NO 3
<211> LENGTH: 24
<212> TYPE: DNA
<213> ORGANISM: Artificial Sequence
<220> FEATURE:
<223> OTHER INFORMATION: universal primer P3
<221> NAME/KEY: modified_base
<222> LOCATION: (1)
<223> OTHER INFORMATION: n=cytidine modified by fluorescent molecule cy3

<400> SEQUENCE: 3
ncagacgaca ccgagatagc agcc                                           24

<210> SEQ ID NO 4
<211> LENGTH: 24
<212> TYPE: DNA
<213> ORGANISM: Artificial Sequence
<220> FEATURE:
<223> OTHER INFORMATION: universal primer P4

<400> SEQUENCE: 4
gggttcgtgg tagagcgtcg gagt                                           24

<210> SEQ ID NO 5
<211> LENGTH: 24
<212> TYPE: DNA
<213> ORGANISM: Artificial Sequence
<220> FEATURE:
<223> OTHER INFORMATION: Tag sequence of synthesized detection probe P2
<221> NAME/KEY: modified_base
<222> LOCATION: (24)
<223> OTHER INFORMATION: n=adenosine modified by amino group
```

<400> SEQUENCE: 5
gccgtgtctg ccgctgggtt atcn                                                    24

TEST PROBES, COMMON OLIGONUCLEOTIDE CHIPS, NUCLEIC ACID DETECTION METHOD, AND THEIR USES

This is a National Phase Application filed under 35 U.S.C. 371 as a national stage of PCT/CN2008/001695, with the filing date of Oct. 6, 2008 an application claiming the benefit from the Chinese Application No. 200810097700.1, filed on May 23, 2008, the entire content of each of which is hereby incorporated by reference in its entirety.

FIELD OF THE INVENTION

The present invention relates to a detection probe, a common oligonucleotide chip, and a nucleic acid detection method, particularly relates to a nucleic acid detection method for nucleic acid detection and sequence analysis, and detection probes and common oligonucleotide chips used thereof.

BACKGROUND OF THE INVENTION

Gene mutation refers to the structure and function change of a genome DNA molecule in compositions or sequence of the base pairs, mainly including base substitution and the deletion or insertion of a small fragment, which is one of the major causes for the genetic diseases. Polymorphism refers to accumulated changes of DNA sequence in human beings during evolution. Gene mutation and polymorphism analysis play very important roles in biomedical researches, particularly in diagnosis and pathological study of genetic diseases. With the development of the human whole-genome sequencing project, it becomes a very urgent task to study gene mutation and polymorphism.

Gene mutations can be determined in many ways. The most classical gene mutation detection technique is nucleic acid hybridization. The traditional methods of nucleic acid molecular hybridization include blot hybridization on a membrane (such as Southern blot, Northern blot), cell hybridization in situ, etc. Due to its high hybridization specificity and high detection sensitivity, the application of nucleic acid hybridization has significantly promoted the development of molecular biology. However, traditional nucleic acid hybridization has a complicated process and too many operation steps, and especially the probes used in the methods are often radioactively labeled, which may easily damage human bodies. Therefore, there is an urgent need for novel, fast and safe detection and analysis technique.

Since PCR technology was developed in 1985, gene mutation detection techniques have been developed rapidly, and many novel detection means and technologies have derived from them, for PCR technology has a powerful in vitro amplification ability for DNA, and the sensitivity and specificity of PCR are greatly enhanced when it is used in combination with a nucleic acid hybridization technology. Many of those techniques are suitable for detecting point mutations, as well as SNPs. Currently, the most popular PCR-based detection technologies include: the methods for detection of known mutations and SNPs include: allele-specific oligonucleotide hybridization (ASO), ligase chain reaction (LCR), TaqMan technology, polymerase chain reaction-based restriction fragment length polymorphism analysis (PCR-RFLP), short tandem repeat length polymorphism (STR), etc.; and the methods for detection of unknown mutations includes: single-strand conformation polymorphism (SSCP), heteroduplex polymorphism analysis (HPA), MALDI-TOF mass spectrometry (matrix assisted laser desorptionion Ization time of flight mass spectrometry), denaturing gradient gel electrophoresis (DGGE), enzyme mismatch cleavage (EMC), dideoxy fingerprinting (ddF), DNA sequencing, etc. The characteristics, principles and applications of those methods have been described in many previous publications. Although these methods can be used to detect the presence of a mutation, most of the methods cannot identify the type of the mutation and can only detect a part of SNP; meanwhile, most of the methods, such as agarose gel electrophoresis, polyacrylamide gel electrophoresis, capillary electrophoresis, high performance liquid chromatography and the like, require detection means such as post PCR processing to analyze and identify the results, and the identification of results is quite complicated. In addition, most of the above detection technologies have complicated processing steps, and only a few of the samples can be detected once, so it is difficult to meet the needs of automation.

DNA sequencing is the most fundamental method for mutation detection. Although DNA sequencing can accurately identify the location and type of a mutation, its practical application is limited for the current gel electrophoresis-based sequencing technology is time-consuming, while the sequencing with automated sequencer is costly.

Biological microarray (or biochip) technology is a fast and high-throughput detection tool that was developed in recent years. In the biological microarray technology, which takes advantage of microarray technology, thousands of biological components (cells, proteins, DNA, etc.) are arranged on a solid phase substrate. The components being detected in a biological sample react with a specific substance on the substrate, and then an appropriate signal (such as fluorescence) is introduced to achieve the purpose of analysis of the biological sample. Biological microarray technology makes some traditional biological analysis means to proceed in a space as small as possible and in a rate as fast as possible. At present, the biochip technology are developing rapidly, and researchers have used a variety of chip technologies, such as gene chip, protein chip, tissue chip, cell chip, lab-on-chip and the like, for large-scale mutation detection and polymorphism screen.

Currently, there are a variety of methods and patent technologies that are based on a DNA chip for gene mutation detections (such as SNP detection) and nucleic acid sequencing analysis, such as Beckman's SNP throughput analysis System (SNPStream assay (Orchid Cellmark/Beckman Coulter)), Illumina's GoldenGate multiple site-specific extension amplification classification system (GoldenGate genotyping assay (Illumina)), Affymetrix's human whole genomic mapping analysis system (GeneChip Human Mapping assays (Affymetrix)), Illumina's Infinium genotyping system (Infinium genotyping assay (Illumina)), Affymetrix's Targeted Genotyping System for drug metabolizing enzymes and transports (DMETs) analysis (Affymetrix), and other mutations (such as SNPs) detection platforms, which are on the basis of the principles of nucleic acid hybridization-based reaction, single base extension reaction (Nikiforov et al., 1994; Bell et al., 2002), allele-specific primer extension and ligation reaction (Gunderson et al., 2005; Landegren et al., 1988), primer ligation reaction (Weiguo Cao, Clinical and Applied Immunology Reviews 2 2001:33-43), restriction enzyme reaction, padlock probe reaction (Xiaoquan Qi, Nucleic Acids Research, 2001, Vol. 29, No. 22 e116); and the relevant gene mutation detections (such as SNP detection) and nucleic acid sequencing analysis as described in other relevant patents, such as U.S. Pat. Nos. 5,427,930, 6,479,242, WO9300447, U.S. Pat. Nos. 5,871,921, 6,858,412, 5,866, 337, etc.

Although those methods have some advantages per se, each also has some defects, such as for the chip technology based on direct nucleic acid hybridization, its non-specific hybridization may result in low resolution, and easily produce a false positive result; while for the chip technologies based on single base extension reaction and allele-specific primer extension reaction, both of them need a multi-color fluorescence system, as well as the amplification, preparation and purification of a target, so that large-scale mutation detections are time-consuming, labor-intensive, etc.

In view of the defects of the existing gene mutation detection (such as SNPs detection) and nucleic acid sequencing analysis, the inventor, on the basis of the multi-year accumulative practical experiences and expertise on the design and manufacture of such products and in combination with the application of related theories, actively does some researches and innovations, so as to create a new detection probe, a common oligonucleotide chip and a nucleic acid detection method, such that the general existing methods for gene mutation and DNA sequencing analysis are improved to be more practical. After continuous study, design, and repeated trial-manufacture and improvement of samples, the present invention, which indeed has a practical value, has been achieved finally.

SUMMARY OF THE INVENTION

The main object of the present invention is to provide a novel detection probe, a common oligonucleotide chip and a nucleic acid detection method to overcome the defects of the existing gene mutation detection and nucleic acid sequencing analysis. The technical problems to be solved are to enable them to meet the purposes of low-cost, high specificity and high sensitivity. And the invention is very suitable for practical use.

The object of the present invention and the solution of the technical problems are achieved by the following technical solutions. The invention provides a detection probe, which is characterized in that the detection probe is composed of detection probe pair of P1 and P2 directing to individual site to be detected. The detection probes P1 and P2 respectively contain the sequence H1 or H2 complementary to the two flanking sequences of the base site to be detected, and each also contains a relevant common oligonucleotide sequence H3 or H4, and P1 or P2 further contains at least a specific Tag sequence. The detection probe pair of P1 and P2 can be ligated into one single probe by the following steps: the detection probe pair P1 and P2 anneals and hybridizes to a nucleic acid sample to be detected; a gap is generated between the probes P1 and P2 that corresponds to the base at the base site to be detected, by hybridizing H1 and H2 to the two flanking sequences of the base site to be detected; the annealed reaction system is divided into four reaction systems of A, T, G and C equally, to which dATP, dTTP, dGTP and dCTP are added respectively; the base complementary to that at the base site to be detected will fill the gap in the presence of DNA polymerase and DNA ligase, and thus the detection probe pair P1 and P2 is ligated into one single probe.

The object of the present invention and the solution of the technical problems can also be achieved by the following technical means.

As to the detection probes mentioned above, they further contain an additional probe P2', which contains the sequence H1 or H2 complementary to one of the two flanking sequences of the base site to be detected, a relevant common oligonucleotide H3 or H4, a specific Tag sequence, and a sequence H5 complementary to the insertion sequence in the insertion site of the sample to be detected.

As to the detection probes mentioned above, the probe P1 or P2 further contains at least a biotin-labeled molecule, and a spacer between the biotin-labeled molecule and the nucleotide sequence of the probe.

As to the detection probes mentioned above, the spacer is a carbon spacer or a non-carbon spacer.

As to the detection probes mentioned above, the non-carbon spacer is polyethylene glycol, polyA or polyT.

As to the detection probes mentioned above, the detection probes can be applied to the re-sequencing of a target nucleic acid sequence, the detection and analysis of the mutation sites and the insertion/deletion sites of a known nucleic acid sequence, and the genotyping detection of a pathogenic microorganism.

The object of the present invention and the solution of the technical problems can also be achieved by the following technical solutions. The invention provides a common oligonucleotide chip, which is divided into four equal regions of A, T, G and C. The oligonucleotide sequences identical with the Tag sequences of corresponding detection probes are spotted on individual site of each region.

As to the common oligonucleotide chip mentioned above, it can be applied to the re-sequencing of a target nucleic acid sequence, the detection and analysis of the mutation sites and the insertion/deletion sites of a known nucleic acid sequence, and the genotyping detection of a pathogenic microorganism.

The object of the present invention and the solution of the technical problems can also be achieved by the following technical solutions. To achieve the object mentioned above, the invention provides a nucleic acid detection method based on the universal oligonucleotide microarray, comprising the following steps: ① preparation of a nucleic acid sample to be detected; ② preparation of detection probes, the detection probes are composed of a detection probe pair P1 and P2 directing to an individual site to be detected, P1 and P2 each contains the sequence H1 or H2 complementary to one of the two flanking sequences of the base site to be detected, a relevant common oligonucleotide H3 or H4, and P1 or P2 also contains at least a specific Tag sequence; ③ each of the probe pairs P1 and P2 is allowed to anneal and hybridize to the nucleic acid sample, and a gap is generated between the probes P1 and P2 which correspond to the base at base site to be detected; ④ the annealed reaction system is divided into four equal reaction systems of A, T, G and C, to which dATP, dTTP, dGTP and dCTP are added respectively, the base complementary to the base at base site to be detected fills the gap in the presence of DNA polymerase and DNA ligase, and thus the detection probe pair of P1 and P2 is ligated into one single probe; ⑤ purification of the above ligated probe; ⑥ amplification of the purified probe; ⑦ preparation of a common oligonucleotide chip, dividing each chip into four hybridization regions of A, T, G and C, and the oligonucleotide sequences identical with the Tag sequences on the corresponding probes are spotted on individual site of each region; ⑧ the four hybridization regions of A, T, G and C of the above oligonucleotide chip hybridize to the probes in the four corresponding amplified reaction systems respectively; and ⑨ the results detection and analysis of the chip.

As to the nucleic acid detection method as mentioned above, in the steps of preparation of the detection probes, another probe P2' is prepared, which contains the sequence H1 or H2 complementary to one of the flanking sequences of the base site to be detected, a relevant common oligonucleotide H3 or H4, a specific Tag sequence, and a sequence H5 complementary to the insertion sequence in the insertion site of the sample to be detected.

As to the nucleic acid detection method as mentioned above, the nucleic acid sample to be detected is animal or plant chromosome DNA, PCR amplification products of target nucleic acid, mitochondrial DNA, cDNA, or bacterial or viral DNA or RNA.

As to the nucleic acid detection method as mentioned above, the probe P1 or P2 further contains at least a biotin-labeled molecule at the terminal end that is not ligated, and a spacer between the biotin-labeled molecule and the nucleotide sequence of the probe to facilitate the subsequent purification and amplification of the probe.

As to the nucleic acid detection method as mentioned above, the spacer is a carbon spacer, polyethylene glycol, polyA or polyT.

As to the nucleic acid detection method mentioned above, the step of purification of the probe is carried out by virtue of a streptavidin-coated carrier medium.

As to the nucleic acid detection method as mentioned above, the carrier medium is composed of magnetic particles or polystyrene microspheres.

As to the nucleic acid detection method as mentioned above, the step of amplification of the probe is a symmetric or asymmetric PCR amplification using universal primers.

As to the nucleic acid detection method as mentioned above, if a conventional PCR amplification is carried out by virtue of universal primers, at least one of the universal primers also contains a molecular label at its 5'end. If a asymmetric PCR is carry out by virtue of universal primers, at least one of the universal primers is a limiting primer, the other is a non-limiting primer, and the non-limiting primer also contains a molecular label at its 5'end.

As to the nucleic acid detection method as mentioned above, the molecular label is a non-isotope label or a radioisotope label.

As to the nucleic acid detection method as mentioned above, the non-isotope label is a fluorescent substance label such as a fluorescein molecular (cy3, cy5 or FITC), a metal label such as Hg, a hapten label such as digoxin, an enzyme such as horseradish peroxidase enzyme (HRP), galactosidase, alkaline phosphatase, etc.

As to the nucleic acid detection method as mentioned above, the radioisotope label is 32P or 35S.

As to the nucleic acid detection method as mentioned above, in the step of the result detection and analysis of the chips, the detection results are determined by scanning the chip with single-color fluorescent scanner and determining the presence of the fluorescent signals on the corresponding sites of the four chip regions, or by applying enzyme coloration to the chip.

As to the nucleic acid detection method as mentioned above, it can be applied to the re-sequencing of a target nucleic acid sequence, the detection and analysis of the mutation sites and the insertion/deletion sites of a known nucleic acid sequence, and the genotyping detection of a pathogenic microorganism.

The present invention has obvious advantages and beneficial effects in comparison with the prior art. The present invention provides a nucleic acid detection method based on the universal oligonucleotide microarray, making use of the detection probe pair of P1 and P2 to detect some base site in the nucleic acid sequence. The 5'- and 3'-end sequences of the two probes complement to both of the left and right flanking sequences of base site to be detected respectively. After the probes anneal and hybridize to a template, a gap is generated at the base site to be detected. Since the detection is carried out in four detection tubes, only when a deoxyribose nucleotide added in each tube complements to the base at the base site to be detected, the deoxyribose nucleotide can be introduced to fill the gap in the presence of DNA polymerase. And then, the detection probes P1 and P2 are ligated into one single probe in the presence of DNA ligase, such that the subsequent steps of purification and amplification of the probes can be proceeded. In addition, the present invention is based on the universal chip technology, and divides the chip into four regions, while the Tag sequences spotted on different specific sites on the chip are the same. During hybridization, the amplification systems in the four reaction tubes are independently hybridized to the four regions on the chip respectively. Lastly, the chip is scanned with single-color fluorescent scanner and the presence of the fluorescent signals in the corresponding sites of the four chip regions is detected to determine the detection results, which is very simple. Also, the use of universal Tag sequence on the microarray may rule out the selection and optimization of conditions for the hybridization between the sequence-specific probes and the microarray.

By virtue of the technical solutions as mentioned above, the present invention provides a novel detection probe, a universal oligonucleotide chip and a nucleic acid detection method, which have the following advantages and beneficial effects:

1. Low cost. In the nucleic acid detection method of the present invention, the cost of nucleic acid detection is reduced in the following aspects. Firstly, by using a pair of universal primers that can amplify all of the detection probes, the cost of designing and optimizing a large number of amplification primers based on target sequences as required in multiplex PCR, is saved. Secondly, the present method is based on the universal chip technology, and the site to be detected is located and analyzed by virtue of the Tag sequences present on the detection probes and spotted on the specific sites on the chip, such that the cost of selecting and optimizing the conditions for the hybridization between sequence-specific probes and microarray is saved. Lastly, in the present method, the 5'end of the universal primer P3 or P4 is labeled with fluorescein cy3, cy5 or FITC label, such that a single-color fluorescence label can be introduced during probe amplification to detect the base site to be detected, which causes the cost of scan and result analysis devices required for detection to be further reduced.

2. High specificity. In the nucleic acid detection method of the present invention, the detection probe pair of P1 and P2 specifically identifies the templates of the nucleic acid samples to be detected. In the four separate reaction systems, the gap formed between probes P1 and P2 is filled and ligated. The ligated probe is purified by magnetic particles. All those steps render the method high specificity.

3. High sensitivity. In the nucleic acid detection method of the present invention, the detection signal is amplified not by direct multiplex PCR amplification of the target sequences, but by the following process: the sequences corresponding to the universal primer pair of P3 and P4 are introduced into the sequences of all detection probe pair of P1 and P2 during designing the probe, and during amplification, P3 and P4 are used as universal primers for asymmetric PCR amplification, which not only forms a single chain that facilitates the hybridization to the chip, but also avoids the uncontrollable cross-reactivity caused by the increase of target sequences in the multiple PCR-based methods, such that the detection sensitivity and specificity are further improved.

4. High-throughput detection capability. The nucleic acid detection method of the present invention includes a specific detection probe design method, an amplification system and a chip design method, which make the nucleic acid detection method have high-throughput detection capability. Also, a special chip design system facilitates a new site to be detected and is easily introduced into the chip.

In summary, in the present invention, the high-throughput detections of the bases to be detected and mutation sites are achieved by designing linear detection probe pair of P1 and P2. After the probes and the templates annealed and hybridized, the annealed reaction system is equally divided into four reaction systems of A, T, G and C, to which a corresponding deoxyribose nucleotide, i.e. dATP, dTTP, dGTP or dCTP, is added respectively. Then, the detection probe pair of P1 and P2 in the four reaction systems are ligated into one single probe in the presence of DNA polymerase and DNA ligase, and the ligated probe is purified by virtue of streptavidin magnetic particles. Asymmetric PCR amplification is proceeded by using a pair of single-color fluorescence labeled nucleic acid sequences to amplify the signal for chip hybridization. The chip of present invention is designed to be divided into four regions of A, G, T and C, which correspond to the four reaction systems of A, G, T and C, and the four regions hybridize to the final amplified products of the four reaction systems. After being washed, the microarrays are scanned with single-color fluorescent scanner and the presence or absence of fluorescent signal in the corresponding sites of the four chip regions is detected to determine the base type at the sites to be detected or the genotypes of the mutation sites.

The invention has the above advantages and practical values, which has significant progress in the method, the effect and technology, and produces useful and practical results. It has an outstanding number of improved effects compared with the current methods of gene mutation detection and nucleic acid sequencing and analysis, such that it is more suitable for practical use, and indeed is a novel, progressive, and practical design.

The above descriptions are merely provided for generally describing the technical solutions of the present invention. The preferred examples are given below with reference to the accompanying drawings, such that the technical means of the invention can be better understood, may be implemented in accordance with the contents of the specification, and these and other purposes, features and advantages of the present invention are more clearly understood. The accompanying drawings are listed as follows.

BRIEF DESCRIPTION OF THE FIGURES

FIGS. 2A-2F are flow diagrams showing a nucleic acid detection method based on the universal oligonucleotide microarray of the present invention.

FIG. 3 is a schematic diagram showing a chip according to the nucleic acid detection method based on the universal oligonucleotide microarray of the present invention.

FIG. 4 is a schematic diagram showing the chip result analysis of a nucleic acid detection method for nucleic acid sequence re-sequencing, wherein the method was based on the universal oligonucleotide microarray of the present invention.

FIGS. 6A-6C are schematic diagrams showing the detection probes according to another example of the nucleic acid detection method based on the universal oligonucleotide microarray of the present invention.

FIGS. 7A-7D are flow diagrams showing the nucleic acid detection method according to another example of the nucleic acid detection method based on the universal oligonucleotide microarray of the present invention.

DETAILED DESCRIPTION OF THE INVENTION

To further illustrate the technical means that are adopted to achieve the intended purpose of the present invention and the effects thereof, the following, with reference to the preferred examples and the accompanying drawings, describes the detection probes, universal oligonucleotide chip and nucleic acid detection method provided according to the present invention, and also use thereof and the specific embodiments, structures, features and effects thereof. The details are described as follows.

The principle of the present invention is that, based on the universal oligonucleotide chip, the high-throughput detections of the bases to be detected or mutation sites are achieved by designing linear detection probe pair of P1 and P2. After the probes and the templates are annealed and hybridized, the annealed reaction system is divided into four reaction systems of A, T, G and C. The detection probe pairs P1 and P2 are ligated in the presence of DNA polymerase and DNA ligase. The ligated probe is hybridized to the four hybrid regions of A, T, G and C corresponding to the chips after purification and amplification, and the introduction of a fluorescence signal. The Tag sequences corresponding to the probes are spotted on individual sites in the four regions of the chip. After hybridization and washing, the microarrays are scanned with single-color fluorescent scanner and the presence or absence of fluorescent signal in the corresponding sites of the four chip regions is detected to determine the base type of the sites to be detected or the genotypes of the mutation sites.

Figure 1A:
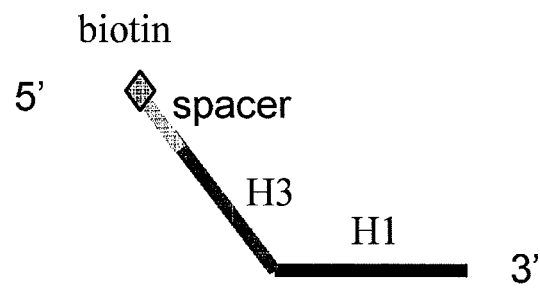
FIGS. 1A-1B are schematic diagrams showing detection probes according to a example of the nucleic acid detection method based on the universal oligonucleotide microarray of the present invention.
Figure 1B:
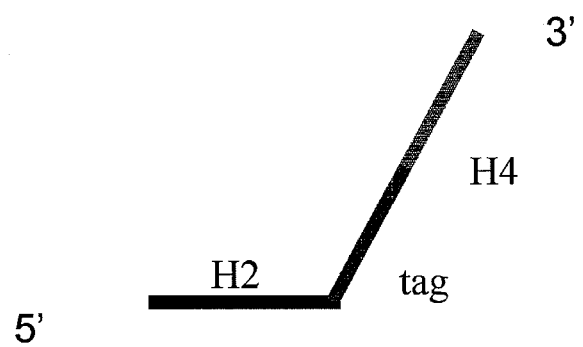

FIGS. 1A-1B are schematic diagrams showing the detection probes according to a example of the nucleic acid detection method based on the universal oligonucleotide microarray of the present invention. For a certain base site to be detected, the method for designing a detection probe is: using two linear probes P1 and P2 to detect the base site. The design of oligonucleotide sequences is illuminated as follows.

As shown in FIG. 1A, the oligonucleotide sequence of the probe P1 designed according to the present invention is composed of three parts of H1, H3 and a spacer, wherein H3, located at the 5'end of the probe P1, is a common oligonucleotide sequence of about 20 nt for symmetrical or asymmetrical PCR amplification of the probe, while H1, located at the 3'end of probe P1, is a sequence of about 20 nt complementary to one of the flanking nucleic acid sequences of the base site to be detected on the template. In addition, in order to purify the probe to facilitate the subsequent procedures, the probe P1 further contains a biotin-labeled molecule at its 5'end. To facilitate the purification and PCR amplification of the probe, a spacer is designed between the biotin-labeled molecule and the 5'end nucleotide of the probe P1. The spacer could be a carbon spacer, or other types of spacers.

As shown in FIG. 1B, the oligonucleotide sequence of the probe P2 designed according to the present invention is composed of three parts of H2, H4 and a tag, wherein the sequence of about 20 nt at the 5'end of probe P2 is the sequence H2 that is complementary to the other flanking nucleic acid sequence of the base site to be detected, while the sequence of about 20 nt at the 3'end of the probe P2 is the sequence H4 that is complementary to the other universal primer P4. The 5'end of this universal primer P4 is labeled with the fluorescein molecule cy3. In addition, the probe P2 contains a specific Tag sequence for the hybridization and identification of a specific site on the chip.

Figure 2A:
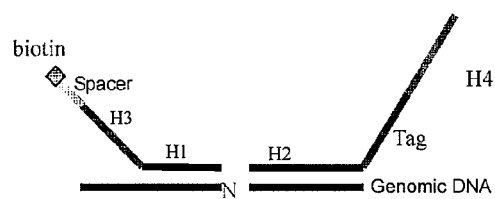

FIGS. 2A-2F are flow diagrams showing a nucleic acid detection method based on the universal oligonucleotide microarray of the present invention. As shown in FIG. 2A, the probes required for detection and the nucleic acid sample undergo a process of annealing and hybridization at an appropriate temperature. After the probes and the template have annealed and hybridized, a gap of one base is generated between the 3'end of the probe P1 and the 5'end of the probe P2, so that the base in the gap exactly corresponds to the base at the base site to be detected.

Figure 2B:
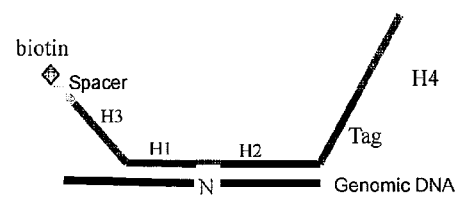

As shown in FIG. 2B, after the probes and the template have annealed and hybridized, if the base added into the reaction system complemented to that at the base site to be detected on the template, the probes P1 and P2 should be ligated into one single probe in the presence of DNA polymerase and DNA ligase. The detailed procedures of filling the gap and ligating the probes are described as follows: The probes required for detection, a DNA template, a nucleic acid sample and a reaction buffer are mixed, and the resulting mixture is divided equally into four reaction tubes, which are labeled with A, T, G or C, respectively; after annealing and hybridization, a gap of one base is generated between the 3'end of the probe P1 and the 5'end of the probe P2, so that the gap corresponds to the base at the base site to be detected; then, to each of the four reaction tubes of A, T, G and C, a corresponding deoxyribose nucleotide, i.e. dATP, dTTP, dGTP or dCTP is added, together with DNA polymerase and DNA ligase required for reaction. Only when the deoxyribose nucleotide added in one of the four reaction tubes complemented to the base at the base site to be detected on the template, the deoxyribose nucleotide can be introduced to the gap formed after the annealing between the probe and the template in the presence of DNA polymerase, so that the process of gap filling is completed; after the above procedures, the probes P1 and P2 are ligated in to a complete probe in the presence of DNA ligase.

Figure 2C:
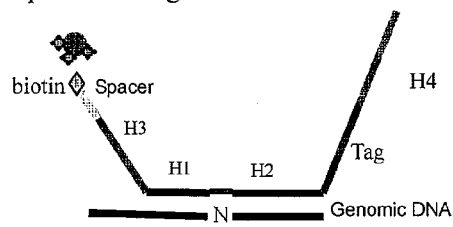
Figure 2D:
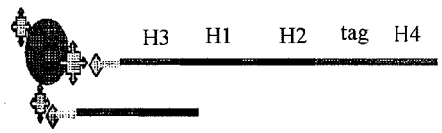

FIGS. 2C-2D show the process of purifying the ligated probe via streptavidin magnetic particles. The detailed procedures are described as follows: after the gap-filling and ligation process of each probe pair of P1 and P2 required for detection, streptavidin-coated magnetic beads are required to purify the complete probe; that is, 2× reaction buffer is added into the four reaction tubes respectively, and the reaction proceeds for 20 min at 180 rpm in a shaker at a constant temperature of 37° C.; after the reaction is completed, the supernatant is removed by magnetic separation, and the magnetic particles are washed three times with wash buffer and stored in ultra-pure water. After purification, the probes that were ligated in each reaction system are captured by the streptavidin magnetic particles.

To amplify the detection signals, the probes in the four reaction systems are amplified by asymmetric PCR respectively, and then hybridized to the corresponding regions on the chip. FIGS. 2E-2F show the amplification process of a probe, wherein symmetric or asymmetric PCR amplification is carried out with the probe that was ligated via the processes of gap-filling and ligation and purified by streptavidin-coated magnetic particles as a template, and the sequences H3 and P4 as a universal primer pair. DNA polymerase and reaction buffer are added, and asymmetric amplification are carried out with the sequence H3 as a limiting primer, and P4 as a non-limiting primer, while P4 has a fluorescent molecule label cy3 at its 5'end. After amplification, a large number of cy3 labeled single-stranded probes are generated. Then, the supernatant is removed by magnetic separation, and hybridized to the corresponding regions on the chip. Since the probe P2 contains a specific Tag sequence, after the PCR amplification, the sequence of the cy3 labeled amplification product contains a Anti-Tag sequence complementary to the Tag sequence. The amplification products of the four systems hybridize to the corresponding individual regions on the chip on which the Tag sequences were spotted. The chips are washed and scanned to determine the detection results.

FIG. 3 is a schematic diagram showing a chip according to the nucleic acid detection method based on the universal oligonucleotide microarray of the present invention. Each chip is divided into four regions of A, T, G and C for hybridizing to the probes in the four reaction systems of symmetric or asymmetric PCR amplification respectively. The corresponding site on each region is spotted a sequence identical with the Tag sequence of the probe P2 for the identification and location of this specific base site to be detected. Each of the four regions is used for hybridizing to the amplification product to which the corresponding base was added. As shown in FIG. 3, 15 Tag sequences are spotted, for example, to illuminate the partitions of a chip. The corresponding sites of these 15 Tag sequences are used to detect the 15 base sites to be detected. As the number of the Tag sequences spotted on each region increases, the detection throughput of the technology also increases. Therefore, this technology can realize ultra-high detection throughput.

The universal oligonucleotide microarray provided by the present invention can be applied to the re-sequencing of a target nucleic acid sequence. The schematic diagram showing the chip result analysis for the re-sequencing of a nucleic acid sequence is shown in FIG. 4. If the fluorescence signal appears on the site 1 of region A of the chip, it suggests that the sequences of the detection probes H1 and H2 corresponding to the Tag sequence on site 1 are present in the target nucleic acid sequence, and the base at the site to be detected in the target nucleic acid sequence is T. If the fluorescence signal appears on the site 2 of region G of the chip, it suggests that the sequences of the detection probes H1 and H2 corresponding to the Tag sequence on site 2 are present in the target nucleic acid sequence, and the base at the site to be detected in the target nucleic acid sequence is C. If the fluorescence signal appears on the site 3 of region T of the chip, it suggests that the sequences of the detection probes H1 and H2 corresponding to the Tag sequence on site 3 are present in the target nucleic acid sequence, and the base at the site to be detected in the target nucleic acid sequence is A.

Figure 5:
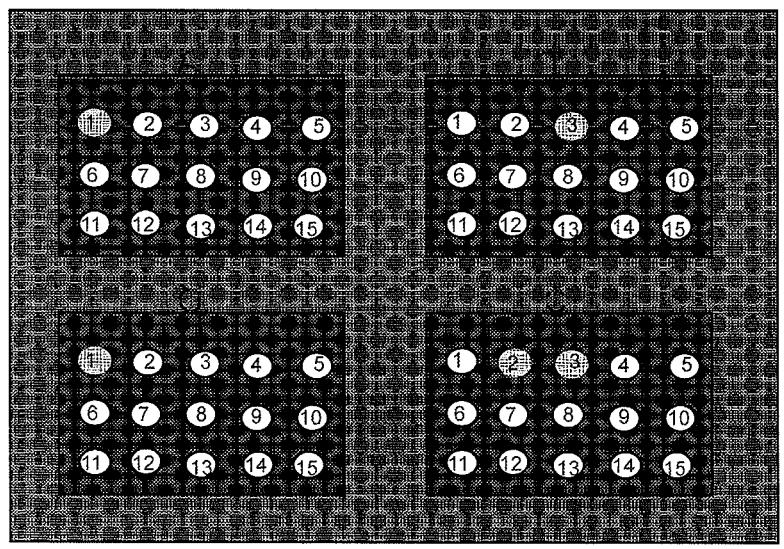
FIG. 5 is a schematic diagram showing the chip result analysis of a nucleic acid detection method for SNP site detection, wherein the method was based on the universal oligonucleotide microarray of the present invention.

The universal oligonucleotide microarray provided by the present invention can be applied to the detection of the mutation of a known nucleic acid sequence, such as the detection of SNP mutation sites. The schematic diagram showing the chip result analysis of the detection of SNP mutation sites is shown in FIG. 5. The sites 1, 2 and 3 corresponds to the three mutation sites of SNP1, SNP2 and SNP3, respectively. If the results of chip scan are the same as shown in the figure, i.e. the fluorescence signal appears on the site 1 of regions A and G, the site 2 of region C, and the site 3 of regions C and T, the genotype of SNP1 site is T/C heterozygote, the genotype of SNP2 site is G/G homozygote, and the genotype of SNP3 site is G/A heterozygote.

In addition, the universal oligonucleotide microarray provided by the present invention can be applied to the detection and analysis of insertion/deletion sites. The insertion/deletion polymorphism sites of a short fragment (one or several bases) are genotyped using three probes of P1, P2'and P2, whose sequence design are as shown in FIG. 6A-6C. The oligonucleotide sequence of the probe P1 as shown in FIG. 6A is composed of three parts of H1, H3 and a spacer, and contains a biotin label at its 5'end. The oligonucleotide sequence of the probe PT as shown in FIG. 6B is composed of four parts of H2, H4, H5, and a tag. The oligonucleotide sequence of the probe P2 as shown in FIG. 6C is composed of three parts of H2, H4 and a tag'. Among them, H1 is a sequence complementary to one of the flanking sequences of the insertion/deletion site on the template; H5 is a sequence at the 5' end of the probe P2' which is complementary to the sequence of an insertion polymorphism site; and H2 is a sequence complementary to the other of the flanking sequences of the insertion/deletion site on the template. H5 is a sequence that is complementary to the sequence of one or more bases at the insertion polymorphism site, and is only present at the 5' end of the probe P2' rather than the 5' end of the probe P2. Thus the probes P1 and P2' are used to carry out genotyping detection of the insertion template, while the probes P1 and P2 are used to carry out genotyping detection of the deletion template. In addition, H3 and H4 are a pair of relevant common oligonucleotide sequences that are used to amplify the probes. The probes P2' and P2 each further contains a specific Tag sequence for the hybridization and identification of a specific site on the chip.

FIGS. 7A-7D are flow diagrams showing the nucleic acid detection method according to this example. In the processes as shown in FIGS. 7A and 7B, the probes required for detection and the template are allowed to anneal and hybridize at an appropriate temperature, with the base adjacent to the insertion/deletion mutation site on the template as the base corresponding to the gap generated after the annealing of the probe and the template. After the probes and the template annealed and hybridized, a gap of one base is generated between the 3' end of the probe P1 and the 5' end of the probe P2 or P2'.

As shown in FIGS. 7C and 7D, after the probes and the template annealed and hybridized, if the base added into the reaction system is complementary to that at the gap generated after annealing of the probe and the template, the probes P1 and P2 or P2' should be ligated into one single probe in the presence of DNA polymerase and DNA ligase. The subsequent purification, amplification and hybridization processes of the probe are the same as those of the detection procedures described above.

Figure 8:
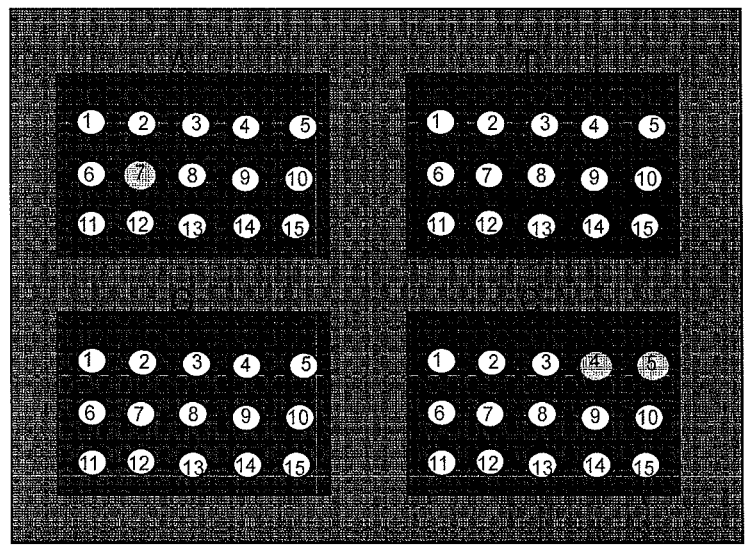
FIG. 8 is a schematic diagram showing the chip result analysis of a nucleic acid detection method for insertion/deletion site detection, wherein the method was based on the universal oligonucleotide microarray of the present invention.

The schematic diagram of the chip result analysis of the insertion/deletion site detection is shown in FIG. 8. When an insertion/deletion site is detected, two sites of each region on a chip are used to detect one insertion/deletion site. When the sites 4 and 5 on a chip are used to detect an insertion/deletion site X, the Tag sequence spotted on site 4 corresponds to the Tag sequence on a insertion site detection probe P2', and the Tag' sequence spotted on site 5 corresponds to the Tag' sequence on a deletion site detection probe P2, the base corresponding to the gap generated after the annealing of the probe and the template is G; When sites 6 and 7 on a chip are used to detect another insertion/deletion site Y, the Tag sequence spotted on site 6 corresponds to the Tag sequence on an insertion site detection probe P2', and the Tag' sequence spotted on site 7 corresponds to the Tag sequence on a deletion site detection probe P2, the base corresponding to the gap generated after the annealing of the probe and the template is T. As shown in FIG. 8, if the fluorescence signal appears on sites 4 and 5 of the region C, the genotype of the site X is an insertion/deletion heterozygote; and if the fluorescence signal appears only on the site 7 rather than the site 6 of the region A, the genotype of the site Y is an insertion/deletion homozygote.

In the following examples, the CYP3A4*17, c.566T>C (F189S) mutation present in the fragment of the cloned human genomic drug metabolism enzymes P450 gene are detected with the universal oligonucleotide microarray of the present invention. The specific steps are as follows.

(1) Design and synthesis of the detection probes: the detection probe pair required has the following sequences.

(2) Ligation of the detection probes P1 and P2: the gap between the detection probes P1 and P2 is filled via filling and ligation. The reaction system is formulated as follows: the probes P1 and P2, each 10 fmol; template, 1-5 ng; DNA polymerase and DNA Ligase, each 0.1 μl; and 10× reaction buffer was are mixed. The resulting mixture is equally divided into four reaction tubes, into which 0.1 μl of dATP, dTTP, dGTP and dCTP are added respectively, and ultra-pure water is supplemented up to 20 μl. The reaction is carried out under the following reaction conditions: 5 min at 94° C.; 30 cycles of 1 min at 94° C., and 2 min at 57° C.; and 5 min at 57° C.

(3) Purification of the Ligated Probe:

a. after the ligation reaction is completed, the four reaction systems are heated at 94° C. for 10 min, and then quenched on ice.

b. 2× purification buffer and 5 μl streptavidin magnetic particles are added into the four reaction systems, and then the reaction is allowed to proceed at 180 rpm in a shaker at a constant temperature of 37° C. for 20 min. After the reaction is completed, the supernatant is removed by magnetic separation. Then, the magnetic particles are washed twice with 80 μl wash buffer. Again, the supernatant is removed by magnetic separation.

c. The magnetic particles are re-suspended in 5 μl ultra-pure water.

(4) PCR amplification of the purified probe: the amplification system is as follows: 1 μl re-suspended magnetic particles as a template; the universal primers P3 and P4, each 0.1 μl; 7.5 μl of 2×Taq PCR mastermix; and 6.5 μl of dH2O, so that the reaction system is 15 μl. The PCR amplification is allowed to proceed under the following conditions: 5 min at 94° C.; 20 cycles of 1 min at 94° C., 1 min at 55° C., 1 min at 72° C.; 5 min at 72° C., and stored in 4° C. After the reaction is completed, the supernatant in each of the four systems is removed by magnetic separation for further use.

Figure 9A:
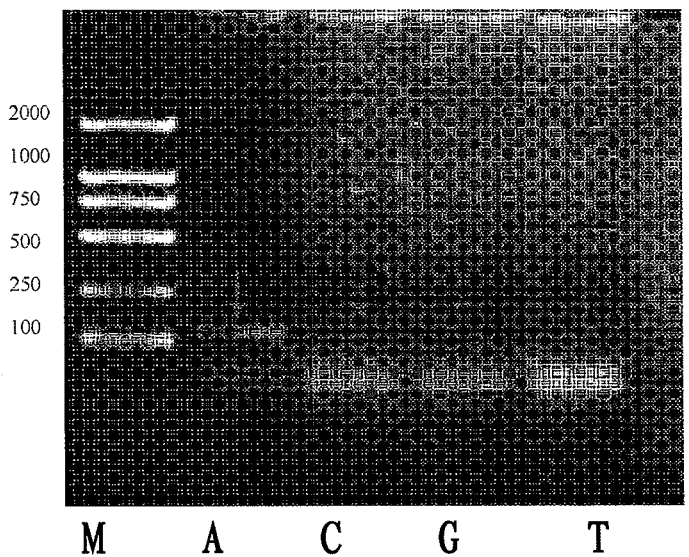
FIGS. 9A-9C are validation electrophoresis photos showing the detection result of the mutation sites present in the gene fragment of the cloned human genomic drug metabolism enzymes P450 gene, wherein the mutation sites were detected by the nucleic acid detection method based on the universal oligonucleotide microarray of the present invention.
Figure 9B:
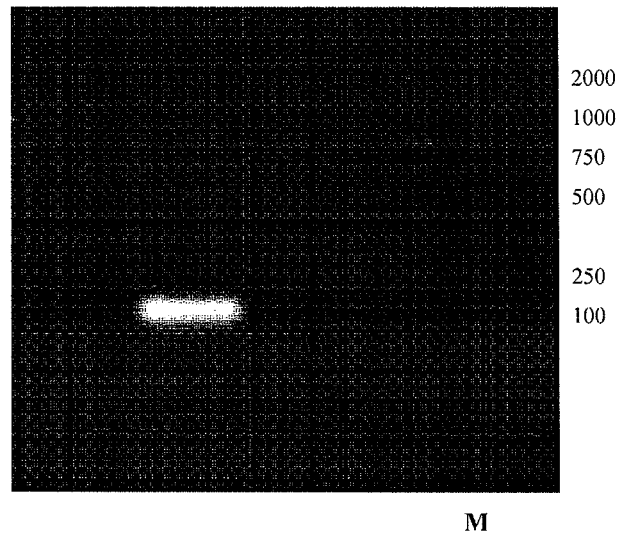
Figure 9C:
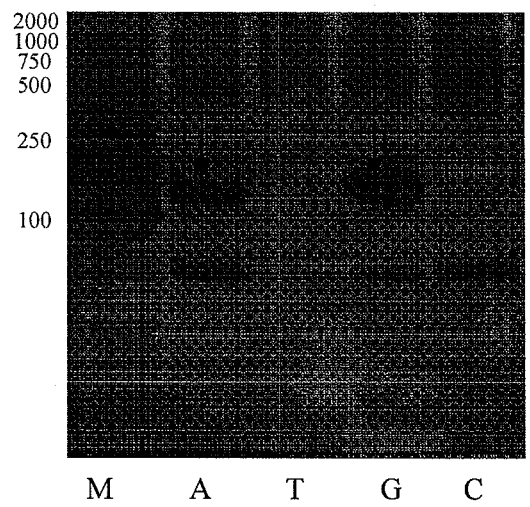

(5) The validity of the reaction system is verified with 7 μl PCR product via 1.5% agarose gel electrophoresis or 12% PAGE gel electrophoresis. The predicted results are that, when the wild-type (T) template is detected, the ligation of probes P1 and P2 and the subsequent PCR amplification using the ligated product as template can be carried out only in the reaction system A, and thus the PCR product should only appear in the lane of the reaction system A. When the wild-type (T) and mutant (G) templates are mixed up and detected, the ligation of probes P1 and P2 and the subsequent PCR amplification using the ligated product as template can be carried out only in the reaction systems A and G, and thus the PCR product should only appear in the lanes of the reaction systems A and G. The results are shown in FIGS. 9A-9C.

(6) Preparation of the oligonucleotide chip: aldehydized chip bases are prepared and divided into four hybridization regions in accordance with the requirements of the claims, and the corresponding Tag sequence is spotted in each region. The chip bases are dried for further use.

(7) Hybridization of the probes: the PCR amplification products of the step (5) are mixed with hybridization buffer, and allowed to hybridize to the corresponding chip regions at 60° C. for 4 h. After the hybridization completes, the chips are washed and then spun to dry.

(8) the chip scan and the result analysis: the chips are scanned with a single-color fluorescent scanner, and the results are shown in FIG. 5D. The results are analyzed according to the scan graphs.

FIGS. 9A-9C are the validation electrophoresis photos showing the mutation sites present in the gene fragment of the cloned human genomic drug metabolism enzymes P450 gene, wherein the mutation sites are detected by the nucleic acid detection method based on the universal oligonucleotide microarray of the present invention.

FIG. 9A shows the detection result of the wild-type (T) template of CYP3A4*17, c.566T>C (F189S) mutation present in the fragment of the cloned human genomic drug metabolism enzymes P450 gene. After probe purification and PCR amplification of the four reaction systems, the amplification products are analyzed with 1.5% agarose gel electrophoresis. The lane M is DNA Marker 2000. The Lanes A, C, G and T are the lanes of the four reaction systems respectively. From the figure, it could be seen that there is a band of more than 100 nt in the lane A, while there is no corresponding band in the other three lanes. The results are the same as expected. To verify if the band appeared in the lane A is exactly the band that should appear according to the theory, the band in the lane A is collected, and amplified via PCR with the universal primers P3 and P4. The amplification products are analyzed with 1.5% agarose gel electrophoresis, and the results is shown in FIG. 9B. From FIG. 9B, it could be seen that there is a band at the same position as that of the lane A in FIG. 9A. It demonstrates that the band appeared in the lane A in FIG. 9A indeed is the product of the PCR amplification with the ligated product of probes P1 and P2 as a template and the universal primers P3 and P4 as primers.

FIG. 9C shows the detection result of the mixture of the wild type (T) template of CYP3A4*17, c.566T>C (F189S) mutation present in the fragment of the cloned human genomic drug metabolism enzymes P450 gene, and the mutant (C) template. After the probe purification and PCR amplification of the four reaction systems, the amplification products are analyzed with 12% PAGE gel electrophoresis. The lane M is DNA Marker2000. The Lanes A, C, G and T are the lanes of the four reaction systems, respectively. From the figure, it could be seen that there is a band of more than 100 nt in both of the lanes A and C, while there is no corresponding band in the other two lanes. The results are in accordance with the expectation for the detection of the mixture of the wild type (T) template and the mutant (C) template in the experiment.

Figure 10:
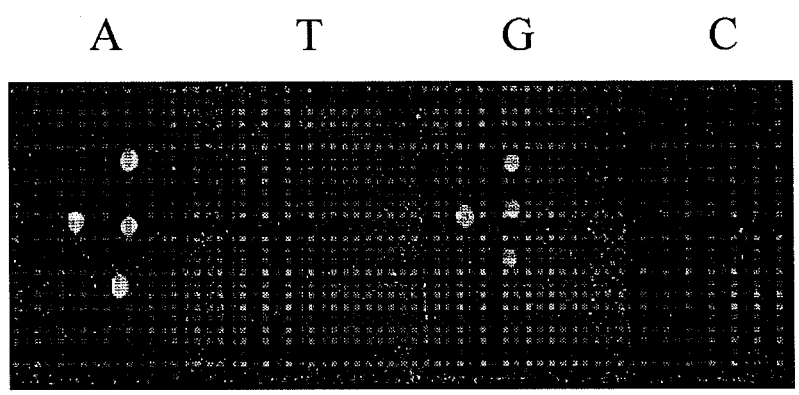
FIG. 10 is a result scanning photo showing the chip hybridization of the mutation sites present in the gene fragment of the cloned human genomic drug metabolism enzymes P450 gene, wherein the mutation sites were detected by the nucleic acid detection method based on the universal oligonucleotide microarray of the present invention.

FIG. 10 is the result scanning photo showing the chip hybridization for the detection of the wild type (T) template of CYP3A4*17, c.566T>C (F189S) mutation present in the fragment of the cloned human genomic drug metabolism enzymes P450 gene, and the mutant (C) template.

In FIG. 10, 6 points are spotted on each region on the chip, wherein two are blank control and four are the Tag sequences. Regions A, T, G and C in the figure are scan results of the hybridization of 6 μl amplification product and the four reaction systems of A, T, G and C, wherein the amplification product is generated via PCR amplification with the purified probes. From the scan results, it could be seen that there is a stronger fluorescence signal only at the point of the four Tag sequence in regions A and G, while there is no fluorescence signal at the corresponding points in the regions T and C. The ratio of the fluorescence signals at the points of the Tag sequences on the positive regions (the regions A and G) and those of the negative regions (the regions T and C) could be up to 10 or more. FIGS. 9A-9C and FIG. 10 suggest that the method can be used as a novel method for SNP analysis.

The above description of the preferred embodiment(s) is merely exemplary and in no way intended to limit the invention. Although the invention has been disclosed with reference to these preferred embodiments as above, the embodiments are not meant to be limiting. Those skilled in the art can make some variations or modifications which are considered as equivalent changes to the techniques disclosed above to achieve equivalent embodiments, without deviating from the scope of the technical solutions of the invention. The technical solutions of the invention encompass any simple varieties, equivalent changes and modifications to the embodiments above on the basis of the technical essentials of the invention, without deviating from the technical solutions of the invention.

The invention claimed is:

1. A nucleic acid detection method comprising the following steps:
    (1) preparing a nucleic acid sample;
    (2) preparing detection probes comprising a detection probe pair (P1 and P2) used for detecting an individual base, wherein each of detection probes P1 and P2 contains either one of two sequences (H1 and H2) respectively complementary to the two flanking sequences of the base site and a relevant common oligonucleotide (H3 or H4), wherein the detection probe pair contains at least a specific Tag sequence, and wherein the base site is in the nucleic acid sample;
    (3) annealing and hybridizing detection probes P1 and P2 to the nucleic acid sample so that an one nucleotide gap is generated between detection probes P1 and P2 on a hybridization complex formed by detection probes P1 and P2 and the nucleic acid sample, thereby obtaining an annealed reaction system, wherein, when the gap is filled by a nucleotide, the nucleotide filled in the gap exactly corresponds to the base at the base site in the nucleic acid sample;
    (4) dividing the annealed reaction system obtained by step (3) into four different equal reaction systems of A, T, G and C by adding only dATP to reaction system A, adding only dTTP to reaction system T, adding only dGTP to reaction system G, adding only dCTP to reaction system C; performing four different ligation reactions by adding a DNA polymerase and a DNA ligase into each of the four different equal reaction systems of A, T, G and C; and forming four different ligation mixtures so that the gap is filled by one of dATP, dTTP, dGTP and dCTP and a ligated probe is produced by ligating detection probes P1 and P2;
    (5) separately purifying the four different ligation mixtures;
    (6) performing four different amplification reactions using the four different ligation mixtures purified in step (5) and forming four different amplification reaction mixtures, wherein one or two of the four different amplification reaction mixtures have an amplification product comprising the ligated product;
    (7) preparing a common oligonucleotide chip comprising immobilized different oligonucleotide probes and dividing the chip into four different hybridization regions of A, T, G and C; wherein the oligonucleotide probes in hybridization region of A comprise the specific Tag sequence and only hybridize to the ligated probe when the gap is filled by dATP, the oligonucleotide probes in hybridization region of T comprise the specific Tag sequence and only hybridize to the ligated probe when the gap is filled by dTTP, the oligonucleotide probes in hybridization region of G comprise the specific Tag sequence and only hybridize to the ligated probe when the gap is filled by dGTP, and the oligonucleotide probes in hybridization region of C comprise the specific Tag sequence and only hybridize to the ligated probe when the gap is filled by dCTP;
    (8) hybridizing each of the four different amplification reaction mixtures to its corresponding hybridization regions of A, T, G, or C on the oligonucleotide chip respectively and producing one or more hybridization signals; and
    (9) detecting and analyzing the one or more hybridization signals obtained from step (8).

2. The nucleic acid detection method according to claim 1, wherein the nucleic acid sample further comprises an insertion sequence and the detection probes further contain an additional probe (P2') which contains a sequence (H1 or H2) complementary to one of the flanking sequences of the base site, a relevant common oligonucleotide (H3 or H4), a specific Tag sequence, and a sequence (H5) complementary to the insertion sequence.

3. The nucleic acid detection method according to claim 1, wherein the nucleic acid sample is a nucleic acid selected from the group consisting of animal or plant chromosome DNA, a PCR amplification product of a target nucleic acid, mitochondrial DNA, cDNA, bacterial DNA, bacterial RNA, viral DNA, and viral RNA.

4. The nucleic acid detection method according to claim 1, wherein one probe of the detection probe pair contains at least a biotin molecule at one of its terminal ends which is not capable of ligating to other probe of the detection probe pair, and a spacer between the biotin molecule and the nucleotide sequence of the probe to facilitate the purification and amplification of the one probe.

5. The nucleic acid detection method according to claim 4, wherein the spacer is selected from the group consisting of a carbon spacer, polyethylene glycol, polyA, and polyT.

6. The nucleic acid detection method according to claim 4, wherein separately purifying the four different ligation mixtures in step (5) is carried out via an interaction between the biotin molecule of the one probe and a streptavidin-coated carrier medium.

7. The nucleic acid detection method according to claim 6, wherein the carrier medium is magnetic particles or polystyrene microspheres.

8. The nucleic acid detection method according to claim 1, wherein the amplification reactions are symmetric or asymmetric PCR amplification reactions which are performed using universal primers complementary to the relevant common oligonucleotide H3 or H4; wherein in the symmetric PCR amplification reactions, at least one of the universal primers also contains a molecular label at its 5' end; or in the asymmetric PCR amplification reactions, at least one of the universal primers is a limiting universal primer, one of the universal primers is a non-limiting universal primer, and the non-limiting universal primer also contains a molecular label at its 5' end.

9. The nucleic acid detection method according to claim 8, wherein the molecular label is selected from the group consisting of a non-isotope label and a radioisotope label; wherein the non-isotope label is selected from the group consisting of a fluorescein molecule, a metal label, a hapten label, and an enzyme; wherein the fluorescein molecule is cy3, cy5 or FITC, the metal label is Hg, the hapten label is digoxin, the enzyme is selected from the group consisting of horseradish peroxidase enzyme (HRP), galactosidase, and alkaline phosphatase; wherein detecting and analyzing the one or more hybridization signals in step (9) comprise scanning the chip with single-color fluorescent scanner and detecting fluorescent signals on the four different hybridization regions of A, T, G, and C when the molecule label on the at least one of the universal primers or the non-limiting universal primer is the fluorescein molecule, or applying enzyme coloration to the chip when the molecular label on the at least one of the universal primers or the non-limiting universal primer is the enzyme; and wherein the radioisotope label is $^{32}P$ or $^{35}S$.

* * * * *

UNITED STATES PATENT AND TRADEMARK OFFICE
CERTIFICATE OF CORRECTION

PATENT NO. : 8,501,459 B2
APPLICATION NO. : 12/994017
DATED : August 6, 2013
INVENTOR(S) : Chao Chen et al.

It is certified that error appears in the above-identified patent and that said Letters Patent is hereby corrected as shown below:

In the Claims:

- Claim 4, column 18, Line 35, after "facilitate the", and before "purification and"

Please insert --subsequent--

Signed and Sealed this
Fifteenth Day of October, 2013

Teresa Stanek Rea
*Deputy Director of the United States Patent and Trademark Office*